US006989163B2

(12) United States Patent
Thompson et al.

(10) Patent No.: US 6,989,163 B2
(45) Date of Patent: Jan. 24, 2006

(54) ARRANGEMENT TO ENHANCE A WOMAN'S SEXUAL SENSITIVITY BY A COMBINATION OF PHYTOESTROGENS, L-ARGININE AND MENTHOL

(75) Inventors: Ronald James Thompson, Ft. Thomas, KY (US); Rhett Larck Frye, Flanders, NJ (US)

(73) Assignee: 40 J's LLC, KY (US)

( * ) Notice: Subject to any disclaimer, the term of this patent is extended or adjusted under 35 U.S.C. 154(b) by 59 days.

(21) Appl. No.: 10/651,615

(22) Filed: Aug. 30, 2003

(65) Prior Publication Data

US 2004/0170708 A1    Sep. 2, 2004

Related U.S. Application Data

(63) Continuation-in-part of application No. 10/004,091, filed on Oct. 23, 2001, now Pat. No. 6,702,733.

(60) Provisional application No. 60/407,748, filed on Sep. 3, 2002.

(51) Int. Cl.
*A61K 35/78* (2006.01)
*A61K 38/00* (2006.01)

(52) U.S. Cl. ............... 424/725; 424/747; 424/757; 424/758; 514/2; 514/969

(58) Field of Classification Search ............ 424/725, 424/757, 747, 758; 514/969, 2
See application file for complete search history.

(56) References Cited

U.S. PATENT DOCUMENTS

| 5,834,513 | A  | * | 11/1998 | Ptchelintsev et al. ....... 514/561 |
| 6,391,869 | B1 | * | 5/2002  | Parks et al. ............ 514/211.07 |
| 6,702,733 | B1 | * | 3/2004  | Thompson ................. 600/38 |
| 2001/0029268 | A1 | * | 10/2001 | Thompson ................ 514/565 |
| 2004/0131579 | A1 | * | 7/2004  | Duraiswami et al. ......... 424/74 |

* cited by examiner

*Primary Examiner*—Christopher R. Tate
(74) *Attorney, Agent, or Firm*—Don Halgren

(57) ABSTRACT

A treatment to induce urothelial sensory nerve re-growth in the female vulvae, comprising a compound of menthol, L-arginine and a phytoestrogen.

9 Claims, No Drawings

ARRANGEMENT TO ENHANCE A WOMAN'S SEXUAL SENSITIVITY BY A COMBINATION OF PHYTOESTROGENS, L-ARGININE AND MENTHOL

BACKGROUND OF THE INVENTION

1. Field of the Invention

The present invention relates to the use of topical phytoestrogens (plant derived estrogens), with a topical combination of menthol and L-arginine topical to induce urothelial sensory nerve re-growth of the normal age-related sensory nerve depletion in women.

2. Prior Art

Estrogens, with the predominant estrogen, estradiol, are produced in the pre-menopausal ovary. A woman's estrus cycle is divided into the Follicular phase, the first fourteen days of the cycle, and the Luteal phase, the last fourteen days of the cycle. During the follicular phase, an ovum is actively developing in the ovarium follicle and estrogen exclusively is produced. During the Luteal phase the ovary produces predominantly progesterone, but also some estrogens. The defining event between the Follicular phase and the Luteal phase is ovulation, the release of ovum from the ovarian follicle.

As sex hormones, estrogens are produced in one tissue, the ovary. They are released into the blood stream, and have their effect on target tissues. Those target tissues have receptors specific for recognition of the estrogen. The estrogens effect on the target tissues is to produce specific tissue growth. Target tissues for estrogens include breast tissue, vaginal tissue, vulvar tissue, endometrial and uterine tissue. Other tissues reported to be target tissues for estrogen include bone, brain, and cardiovascular tissue.

Young women who are not on contraceptive medications have a very high level of estrogen. Women who are on contraceptive medications have a very low level of estrogen, for the intent of contraceptives is to suppress normal ovarian function and prevent ovulation, therefore preventing a possible pregnancy. As each woman normally ages, her level of estrogen declines yearly until menopause, where the ovary is depleted of all ovum, and all estrogen production ceases. "Perimenopause" is the ill-defined time frame before and after menopause. Perimenopause could more appropriately be termed "premenopause", for the estrogen levels for five to ten years before actual menopause (normally age 50) causes a host of signs and symptoms of inadequate estrogen in its target tissues. Perimenopause depression could be inadequate estrogen for its target brain tissue. Osteoporosis is the thinning of trabecular bone associated with genetic predisposition, low calcium intake, inadequate exercise, and low estrogen levels.

The most well recognized sequel of inadequate serum estrogen in both menopausal and perimenopausal women is the lack of adequate stimulation of the target urogenital tissue. These tissues include the vagina, vulvus, urethra, and uterus. Atrophic vulvitis is the "thinning" of vulvar tissues, including the clitoris, clitoral hood, vestibule, labia minora, and labia majora. Normally well estrogenized young women have a cell thickness of twenty to twenty five cells, with the cells each being "plump" and normal. Atrophic vulvitis is diagnosed by the cell thickness being only eight to ten cells thick, where each cell is thin and flat. Bioassays to determine estrogen effectiveness have been performed in castrated rats or rabbits, wherein different estrogens are administered daily for several weeks. A vulvar or a vaginal lavage during such a bioassay is then placed into a glass slide for microscopic examination. A few sparse flat cells indicate a low estrogen effect whereas numerous plump cells indicates a high estrogen effect.

Hormone Replacement Therapy (HRT) has been known for many years. Historically, estrogens as HRT have been used for decades, if not centuries, to treat the vasomotor symptoms (hot flashes, night sweats, insomnia, and depression) of inadequate of inadequate estrogen production associated with menopause. This treatment of estrogen replacement therapy only needs one to two years of duration, for the women's body will accommodate to the high levels of Follicle Stimulating Hormone (FSH), produced by the pituitary gland in the attempts to induce the ovaries to produce estrogens.

In the 1970's, attempts to extend the estrogen mediated youthfulness beyond age 50(menopause), and for women who had their ovaries surgically removed in there thirties or forties, standard therapy was estrogen replacement. This estrogen replacement treatment was intended to continue for ten, twenty, thirty, or even forty years. The theory behind prolonged estrogen replacement therapy was the positive impact on the estrogen target tissues. Estrogen will maintain youthfulness of the vulvar and vaginal tissues by stimulating tissue growth and preventing atrophic vulvitis or atrophic vaginitis caused by inadequate estrogen levels.

A second and more theoretical benefit of prolonged estrogen therapy was to prevent osteoporosis, cardiovascular disease, and even brain disorders such as dementia or cerebral atrophy. The prolonged estrogen therapy also necessitated the intermittent use of progesterone to prevent unopposed stimulation of the endometrium, the lining of the uterus. Initially this HRT, the sequential administration of estrogen and progesterone, was patterned after the normal Follicular/Luteal phases with estrogen given for twenty five days of each calendar month, and progesterone given for the last ten days of estrogen therapy. After the progesterone has been stopped, the patient will have a progesterone-withdraw menstrual period, and sometimes this not will accepted by women in their sixties and seventies!

There are various types of Estrogen, its routes of administration, and the use of pharmakenetics. "Systemic" in parmakenetics means distributed through the entire body system and available to all cells of the body. The predominant normal estrogens produced by the ovaries, estrone, estradiol, and esteriol are only lipid soluble, and therefore not absorbed from the stomach or the intestines. Estradiol is absorbed if injected into the muscle, transdermally absorbed from an "estrogen patch" worn on the stratified squamous skin of the abdomen or buttocks, or applied to the mucous membrane of the vagina or the non-Keratinized epidermis of the vulva. Micronized estradiol orally ingested is partially absorbed from the stomach and the intestine mucosa. Estrogen salts, with the most commonly prescribed being PREMARIN, (pregnant mare urine) are conjugated estrogens that are readily absorbed from the stomach and intestin/mucosa, and are therefore orally active estrogens. A PREMARIN cream is likewise easily absorbed from the vaginal and vulvar tissues.

Phytoestrogens are plant-derived estrogens that are poorly orally active, but have epithelial absorption in the vaginal and vulvar tissues locally, but are not absorbed systematically into the blood stream. This property of local vulvar/vaginal tissue estrogen activity by the phytoestrogens allows treatment and even prevention of atrophic vulvitis/atrophic vaginitis by use of these phytoestrogens typically in the vulvar/vaginal tissues. Phytoestrogens are plant-derived compounds that display estrogenic activity in a bioassay system, previously described hereinabove. Sources of these phytoestrogens include red clover blossom, wild yam extract, black cohosh, soya extract, and licorice root extract.

Estradiol injections or transdermal patches of estradiol provide a constant availability of estradiol in the blood stream. Oral Premarin or oral micronized estradiol provides a large amount of estrogen to the blood stream initially, but this "adequate estrogen" can decay in twelve to twenty four hours. Some patients require oral estrogens every twelve hours (twice per day dosing) to prevent the hot flashes and night sweats. Topical vaginal or vulvar estrogens are effective in the vulvae/vagina tissues to treat or prevent atrophic vulvitis/vaginitis of inadequate estrogen with only once/day application. The topical vaginal/vulvar estrogen creams are ineffective in treatment of hot flashes, night sweats, or insomnia, and are therefore not effective systemically, even if applied several times per day.

Estrogen has implications for breast tissue and breast cancer. Breast tissue is a "target" tissue for estrogen. Breast tissue is also a target tissue for progesterone. Upon removal, breast cancer is analyzed for the presence of estrogen and progesterone receptors. Cancer is the unregulated growth of any tissue. While multiple studies have shown variable associations between breast cancer and estrogen, some show a direct cause and effect relationship, and others showing no cause and effect relationship. The picture is unclear, but there is however, a definite genetic predisposition for breast cancer. A gene BRCA-1 (or 2) may be evaluated to determine each woman's genetic predisposition to breast cancer, and even this is only reported as 10 to 25 percent diagnostic. The unclear cause and effect relationship between the use of systemic estrogen long-term, and the development of breast cancer causes more and more women to decline or abandon estrogen therapy. This decline of the use of HRT has increased the incidence of atrophic vulvitis/vaginitis because of the absolute lack of estrogen. Because of the generalized fear of estrogens, women are even reluctant to use topically active, non-systemic, estrogens to prevent or treat atrophic vulvitis/vaginitis.

Atrophic vulvitis/vaginitis has an effect on a women's sexual sensitivity. Atrophic vulvitis/vaginitis, because of inadequate estrogen, is not only a condition where the epithelial cells are atrophical, but also involves atrophy of the arterioles and the nerves contained within the vulvae and vagina.

Jian Jeny et al, in the 2002 *Supplement to Urology* reported on the important aspects of estrogen and Sexual Sensitivity, "Estrogen Induced Proliferation of Urothelial Cells is Modulated By Nerve Growth Factor (NGF).". The NGF is responsible for the sensory nerve regeneration regulation in the vulvae generally, but in the clitoris specifically (the vagina is devoid of sensory nerves!) This estrogen induced NGF allows perimenopausal, menopausal, and women on contraceptives, who actually develop sensory nerve atrophy, to restore normal sensory nerve functions imperative for normal sexual sensitivity, clitoral arousal and sexual responsiveness.

DESCRIPTION OF THE PRESENT INVENTION

The present invention comprises a combination of menthol and L-arginine, as described in my U.S. Pat. No. 6,322,493, (incorporated herein by reference) with the addition of phytoestrogens for the daily topical application to the female vulvae, and specifically the clitoris to increase sexual sensitivity and sexual responsiveness.

The Menthol acts as a vehicle to allow the absorption of the L-arginine into tissues. Menthol also acts as a vehicle to allow the absorption of phytoestrogens into tissues locally but not systematically. The Menthol also acts to reflexively increase vaginal lubrication through reflex nocieoceptors. The Menthol does act to create an immediate stimulation of vulvae and clitoral tissues through its "cooling" effect and vasodilatation evoking properties.

The L-arginine acts to prolong vasodilatation by inducement of the nitric-oxide synthase pathway. The L-arginine also acts to induce vascular neogenesis through action of endothelial growth factor (EGF) and it acts to induce sensory neogenesis through action of nerve growth factor (NGF). Phytoestrogens in the compound of the present invention act to restore estrogen effects to vulvar tissues to prevent atrophic vulvitis in estrogen deficient women and act to restore estrogens effects to vulvar tissues to treat atrophic vulvitis in estrogen deficient women. The phytoestrogens act to stimulate new sensory nerve growth in women deficient in estrogens. The phytoestrogens effect however, is limited to the vulvar/vaginal mucosa and is not systemically absorbed, therefore there is no estrogen presented to other target tissues such as breast tissue or breast cancer.

The phytoestrogens in the present invention comprise about 1 to about 10% of the compound of the present invention, along with menthol and L-arginine which preferably comprise about 2 to about 3% each. Those phytoestrogens may be selected from the group comprised of red clover blossom, wild yam extract, black cohosh, soya extract and licorice root extract. The compound of the present invention would thus include menthol, L-arginine and a phytoestrogen for topical application to the female vulvae.

The invention thus comprises a treatment to induce urothelial sensory nerve re-growth in the female vulvae, comprising a compound of menthol, L-arginine and a phytoestrogen. The phytoestrogen may comprise red clover blossom, wild yam extract, black cohosh, soya extract, licorice root extract or a combination of all or any of them.

The invention also comprises a method of treating a female vulvae to induce urothelial sensory nerve re-growth in that female vulvae, comprising; admixing a compound of menthol, L-arginine and a phytoestrogen into a topical ointment; and applying the topical ointment to the female vulvae to induce urothelial sensory re-growth. The phytoestrogen may comprise red clover blossom, wild yam extract, black cohosh, wild yam extract, or licorice root extract or any combination of any of them.

The invention mat also comprise a method of enhancing a woman's sexual sensitivity comprising the steps of: admixing a compound of menthol, L-arginine and a phytoestrogen into a topical ointment; and applying said topical ointment to the female vulvae to induce urothelial sensory re-growth and enhance the woman's sexual responsiveness. The phytoestrogen may be selected from one or more of the group comprised of red clover blossom, wild yam extract, black cohosh, soya extract and licorice root extract. The phytoestrogen may preferably comprise about 1 to about 10% of the compound.

We claim:

1. A method for the manual application of an ointment combination for treating a female vulvae to induce urothelial sensory nerve re-growth in that female vulvae, comprising;

admixing an ointment combination of menthol, L-arginine and a phytoestrogen into a topical ointment; and applying said topical ointment to the female vulvae to induce urothelial sensory re-growth.

2. The method as recited in claim 1, wherein said phytoestrogen comprises red clover blossom.

3. The method as recited in claim 1, wherein said phytoestrogen comprises wild yam extract.

4. The method as recited in claim 1, wherein said phytoestrogen comprises black cohosh.

5. The method as recited in claim 1, wherein said phytoestrogen comprises wild yam extract.

6. The method as recited in claim 1, wherein said phytoestrogen comprises licorice root extract.

7. A method for the manual application of a combination ointment for enhancing a woman's sexual sensitivity comprising:

admixing a combination of menthol, L-arginine and a phytoestrogen into a topical ointment; and applying said topical ointment to the female vulvae to induce urothelial sensory re-growth and enhance the woman's sexual responsiveness.

8. The method as recited in claim 7, wherein said phytoestrogen is selected from one or more of the group comprised of red clover blossom, wild yam extract, black cohosh, soya extract and licorice root extract.

9. The method as recited in claim 7, wherein said phytoestrogen comprises about 1 to about 10% of said compound.

* * * * *